United States Patent [19]

Ramsay et al.

[11] Patent Number: 4,921,978

[45] Date of Patent: May 1, 1990

[54] PROCESS FOR THE PREPARATION OF A MACROLIDE COMPOUND

[75] Inventors: Michael V. J. Ramsay, South Harrow; Simon C. Dolan, Harrow, both of United Kingdom

[73] Assignee: American Cyanamid Company, Stamford, Conn.

[21] Appl. No.: 242,227

[22] Filed: Sep. 9, 1988

[30] Foreign Application Priority Data

Sep. 11, 1987 [GB] United Kingdom ................. 8721378

[51] Int. Cl.$^5$ .......................................... C07D 313/00
[52] U.S. Cl. .................................................. 549/264
[58] Field of Search ........................................ 549/264

[56] References Cited

U.S. PATENT DOCUMENTS 4,579,864  4/1986  Linn et al. ............................ 514/450
4,581,345  4/1986  Wyvratt, Jr. ........................... 514/30

FOREIGN PATENT DOCUMENTS 0259686  3/1988  European Pat. Off. ............ 549/264
2166436A  of 0000  United Kingdom .
2176182  of 0000  United Kingdom .

Primary Examiner—Glennon H. Hollrah
Assistant Examiner—Amelia A. Owens
Attorney, Agent, or Firm—Bacon & Thomas

[57] ABSTRACT

A process for preparing the compound of formula (I)

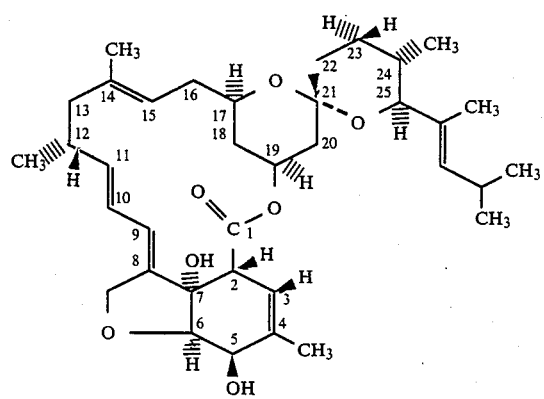

which comprises treating the corresponding 23α-compound sequentially with (i) oxalyl chloride and (ii) 2-mercaptopyridine-N-oxide, a catalytic amount of an organic base, and a thiol.

5 Claims, No Drawings

PROCESS FOR THE PREPARATION OF A MACROLIDE COMPOUND

This invention relates to a novel process for the preparation of a macrolide compound.

The compound of formula (I)

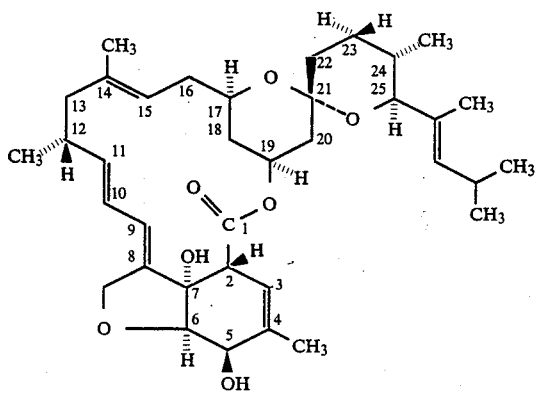

is described in UK Patent Specification 2176182. This compound has anti-endoparasitic, anti-ectoparasitic, anti-fungal, insecticidal, nematicidal and acaridal activity and is useful in combating parasites in animals and humans and pests in agriculture, horticulture, forestry, public health and stored products. The compound may also be of use as an intermediate in the preparation of other active compounds.

The present invention provides a novel and useful 'one-pot' synthesis of the compound of formula (I) from a fermented starting material. The process is convenient to use and provides the compound of formula (I) in good yield.

Thus, we provide a process for preparing the compound of formula (I) which comprises treating a compound of formula (II)

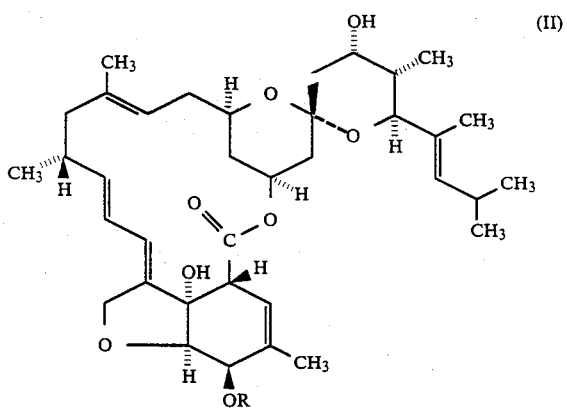

(wherein R represents a hydrogen atom or a projecting group eg acetyl) sequentially with (i) oxalyl chloride and (ii) 2-mercaptopyridine-N-oxide, a catalytic amount of an organic base (eg a tertiary amine such as dimethylaminopyridine) and a thiol (which is preferably a hindered thiol eg trityl thiol), followed, if necessary, by removal of the 5-hydroxy protecting group.

The reaction may be carried out in an inert solvent such as an aromatic hydrocarbon eg toluene. Stage (i) may conveniently be carried out at room temperature and stage (ii) at an elevated temperature eg reflux.

When R is a protecting group it may be any conventional hydroxyl protecting group, for example, as described in "Protective Groups in Organic Synthesis" by Theodora W. Greene (Wiley-Interscience, New York, 1981) and "Protective Groups in Organic Chemistry" by J. F. W. McOmie (Plenum Press, London, 1973). Such groups may be introduced and removed using standard procedures. Thus for example an acyl group such as an acetyl group may be removed by basic hydrolysis e.g. using sodium or potassium hydroxide in aqueous alcohol. Acetal groups such as tetrahydropyranyl may be removed for example, using acid hydrolysis (using an acid such as acetic or trifluoroacetic acid or a dilute mineral acid). Silyl groups may be removed using fluoride ions (e.g. from a tetraalkylammonium fluoride such as tetra-n-butylammonium fluoride), hydrogen fluoride in aqueous acetonitrile or an acid such as p-toluene sulphonic acid (e.g. in methanol). Arylmethyl groups may be removed by treatment with a Lewis acid (e.g. boron trifluoride-etherate) in the the presence of a thiol (e.g. ethanethiol) in a suitable solvent such as dichloromethane at e.g. room temperature.

The compound of formula (II) in which R represents a hydrogen atom is hereinafter referred to as 'Factor A'. This compound may be obtained using the fermentation and isolation methods described in UK Patent Specification No 2166436A. Compounds of formula (III) in which R represents a protecting group may be prepared from Factor A according to methods described in the aforementioned books by Greene and McOmie. Thus, for example, an acetyl group may be introduced using an acetylating agent such as acetic acid or a reactive derivative thereof, such as an acetyl halide (e.g. acetyl chloride), anhydride or activated ester, or a reactive derivative of a carbonic acid, $CH_3OCOOH$ or thiocarbonic acid $CH_3OCSOH$.

Acetylations employing acetyl halides and anhydrides may if desired be effected in the presence of an acid binding agent such as a tertiary amine (e.g. triethylamine, dimethylaniline or pyridine), inorganic bases (e.g. calcium carbonate or sodium bicarbonate), and oxiranes such as lower 1,2-alkylene oxides (e.g. ethylene oxide or propylene oxide) which bind hydrogen halide liberated in the acetylation reaction.

Acetylation employing acetic acid is desirably conducted in the presence of a condensing agent, for example a carbodiimide such as N,N'-dicyclohexylcarbodiimide or N-ethyl-N'γ-dimethylaminopropylcarbodiimide; a carbonyl compound such as carbonyldiimidazole; or an isoxazolium salt such as N-ethyl-5-phenylisoxazolium perchlorate.

An activated ester may conveniently be formed in situ using, for example, 1-hydroxybenzotriazole in the presence of a condensing agent as set out above. Alternatively, the activated ester may be preformed.

The acetylation reaction may be effected in aqueous or non-aqueous reaction media, conveniently at a temperature in the range −20° to +100° C., e.g. −10° to +50° C.

The invention is illustrated but not limited by the following Preparations and Examples in which temperatures are in °C.

PREPARATION 1

Factor A 5-acetate

Factor A (3.0 g) in pyridine (20 ml) at −5° was treated with acetic anhydride (8 ml) and the resulting solution left at 3° for 20 hr. Benzene (100 ml) was added and the solution concentrated in vacuo. The residual oil was chromatographed over silica using dichloromethane:acetone (40:1) as eluent to give Factor A 5-acetate (2.06 g), containing 10% Factor A 5,23-diacetate. The compounds were separated by reverse-phase preparative hplc to give the title compound (79% recovery), $\lambda_{max}$ (EtOH) 244.5 nm ($E_1^1$ 462), $\delta$ (CDCl$_3$) includes 2.14 (s; 3H), m/z includes 654, 594 and 576.

EXAMPLE 1

23-Desoxy Factor A (1) 23-Desoxy Factor A 5-acetate

To a stirred solution of Factor A 5-acetate (500 mg) in toluene (10 ml) was added oxalyl chloride (0.13 ml). After 90 min the mixture was then added, dropwise, to a refluxing solution of toluene (15 ml), 2-mercaptopyridine-N-oxide (0.34 g), trityl thiol (0.84 g) and dimethylaminopyridine (trace). After two hours the cooled mixture was diluted with ethyl acetate (100 ml) and washed successively with 2N hydrochloric acid, saturated sodium bicarbonate and dried over sodium sulphate and the solvent removed. The residue was chromatographed over a column of silica (Merck Art 9385; 100 ml) made up in dichloromethane/ethyl acetate (15:1) and eluted with the same solvent. Appropriate fractions of the major component were combined and the solvent removed to leave the title compound as a foam (200 mg). $[\alpha]_D^{22}+144°$ (c. 0.43 chloroform), $\lambda_{max}$ (ethanol) 245.5 nm ($\epsilon$ 29650), $\lambda_{max}$ (CHBr$_3$) 3420–3340 (OH), 1732 (acetate), 1710 cm$^{-1}$ (carbonyl), $\delta$(CDCl$_3$) include 0.68 (d, 5 H$_z$, 3H), 2.16 (s, 3H), 3.32 (m, 1H).

(ii) 23-Desoxy Factor A

Aqueous sodium hydroxide (13.2 ml) was added dropwise to a solution of 23-desoxy Factor A 5-acetate (8.04 g) in methanol (200 ml) at 3°. After stirring at 0°–5° for 2¼ hours the reactive mixture was diluted with ethyl acetate (1 liter), washed with water (1 liter) and subsequently with water (3×500 ml) and saturated brine (500 ml) and dried over sodium sulphate. The solvent was evaporated and the resultant yellow foam purified by silica gel chromatography (Merck Art 9385, 300 g). The foam was loaded onto the column with ethyl acetate:petroleum ether (3:7) and eluted with the same solvent system to give the title compound as a white foam (6.3 g). $\delta$ (CDCl$_3$) include 3.27 (m; 1H), 3.42 (d9; 1H), 3.54 (m, 1H) and 4.29 (t6; 1H), m/z include 596, 578, 560, 468, 450, 356, 314, 299, 249, 248, 221 and 151.

We claim:

1. A process for preparing the compound of formula (I)

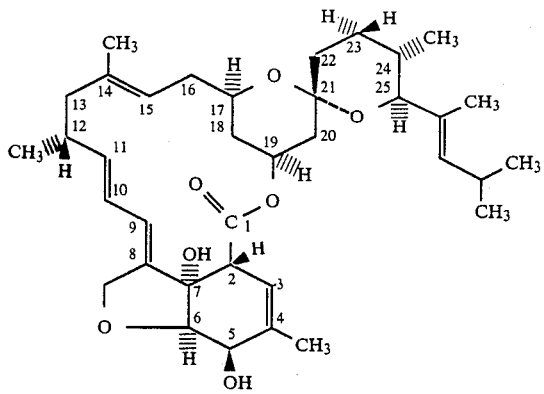

which comprises treating a compound of formula (II)

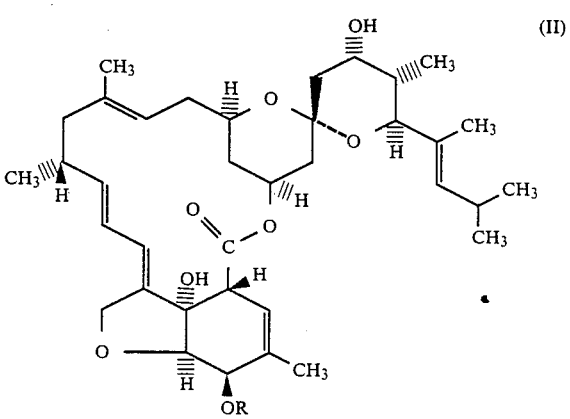

(wherein R represents a hydrogen atom or a protecting group) sequentially with (i) oxalyl chloride and (ii) 2-mercaptopyridine-N-oxide, a catalytic amount of a tertiary amine, and a thiol, followed if necessary by removal of the 5-hydroxy protecting group.

2. A process according to claim 1 in which the thiol is trityl thiol.

3. A process according to claim 1 in which the tertiary amine is dimethylaminopyridine.

4. A process according to claim 1 in which R is an acetyl group in the compound of formula (II).

5. A process for preparing the compound of formula (I)

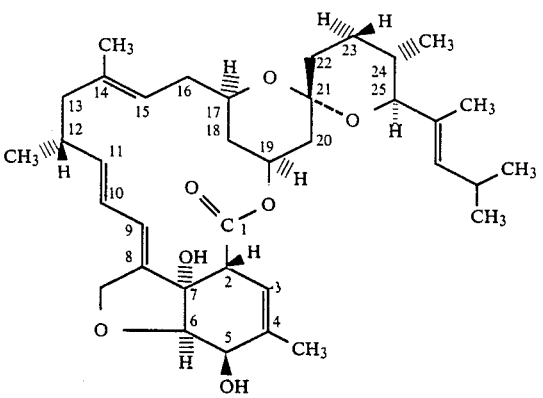

which comprises treating a compound of formula (II)

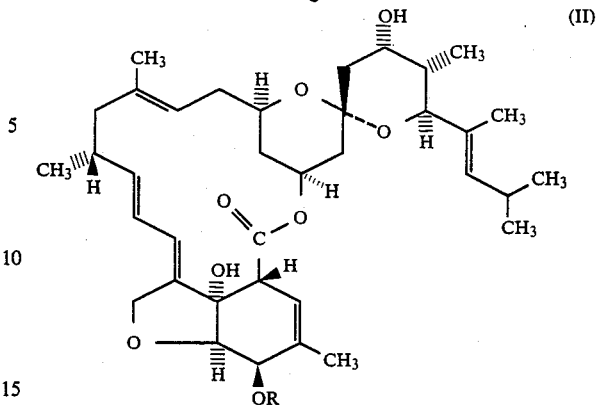
wherein R represents a hydrogen atom or a protecting group, sequentially with (i) oxalyl chloride and (ii) 2-mercaptopyridine-N-oxide, a catalytic amount of dimethylaminopyridine, and trityl thiol, followed if necessary by removal of the 5-hydroxy protecting group.
* * * * *